United States Patent [19]

Ersek et al.

[11] Patent Number: 5,067,965
[45] Date of Patent: Nov. 26, 1991

[54] BIO-OSMOTIC GEL FOR IMPLANT PROSTHESES

[75] Inventors: Robert A. Ersek, Austin, Tex.; Arthur A. Beisang, Arden Hills; Arthur A. Beisang, III, Shoreview, both of Minn.

[73] Assignee: Bioplasty, Inc., St. Paul, Minn.

[21] Appl. No.: 496,234

[22] Filed: Mar. 20, 1990

[51] Int. Cl.$^5$ .................. A61F 2/54; A61M 36/00; A61N 5/00
[52] U.S. Cl. .......................... 623/66; 623/8; 623/11
[58] Field of Search ............ 623/7, 8, 11, 12, 66

[56] References Cited

U.S. PATENT DOCUMENTS

| | | | |
|---|---|---|---|
| 4,138,382 | 2/1979 | Polmanteer | 623/7 |
| 4,731,081 | 3/1988 | Tiffany et al. | 623/8 |
| 4,773,909 | 9/1988 | Chaglassian | 623/7 |
| 4,965,253 | 10/1990 | Goldberg et al. | 604/28 |
| 4,995,882 | 2/1991 | Destouet et al. | 623/8 |

*Primary Examiner*—Randall L. Green
*Assistant Examiner*—Paul Prebilic
*Attorney, Agent, or Firm*—Haugen and Nikolai

[57] ABSTRACT

An improved bio-osmotic gel for filling implant lumens consisting substantially of an amount of a bio-compatible organic polymer and a solution of bio-compatible salt is disclosed which exhibits osmotic qualitites closely paralleling that of human body serum and improved radiolucency with respect to silicone oil and saline. The bio-osmotic gel can contain a polymer having the empirical formula $[(CHCH_2)_2N(CH_2)_3CO]_n$ i.e. polyvinylpyrrollidone. The bio-compatible salt can be made of a low Z value salt such as sodium bicarbonate, sodium acetate, or sodium lactate. The gel material should have an osmolarity between 250 and 350 milliosmoles and have an X-ray absorption under standard exposure approximately equal to that of breast tissue such that processed mammographic X-ray film will have an optical density of 1.2 to 1.3 and an average penetrance of between 9.2 and 30.0 milliroentgens.

15 Claims, No Drawings

BIO-OSMOTIC GEL FOR IMPLANT PROSTHESES

BACKGROUND OF THE INVENTION

I. Field of the Invention

The present invention is generally directed to tissue contour modifying implantable prostheses for use in plastic and reconstructive surgery and, more particularly, to a bio-compatible, excretable gel containing an organic polymer material for use within a flexible prosthesis membrane.

II. Discussion of the Related Art

Implantable silicone and other plastic prosthesis materials for correcting contour defects and form limitations in the human body have been in use since at least the early 1950's. This procedure has been most frequently used for breast reconstruction, either following traumatic or surgical loss of the breast tissue, as through radical mastectomy, or to correct developmental hypoplasia.

Typically such an implant has consisted of a flexible outer shell member made from silicone rubber, polyurethane or other known durable bio-compatible polymer which has an elastic memory and is configured to a shape dedicated to provided the desired bodily contour. The generally hollow shell member may consist of a single layer or double layer in which one shell is placed inside the other.

Many substances have been used to fill the lumen of the implant. Examples of these include normal saline, foam pads and silicone oil or silicone gel. Each of the prior materials, however, exhibit at least one major drawback. Saline, for example, is a poor lubricating agent and such prostheses filled only with saline have been known to undergo accelerated shell breakdown and rupture due to friction of the inner shall rubbing against itself. Molded foam inserts enjoyed a relatively short period of popularity because such materials were found to rapidly calcify after implantation in the body.

After a considerable period of time, silicone oil remains the most commonly used filling material. With respect to most implant prostheses including breast implants, the filler is normally utilized in the form of a partially vulcanized silicone which is sealed inside the lumen prior to implant. This material has enjoyed a long period of use principally because of two desirable properties. Silicone oil is a natural lubricant and this tends to prevent shell breakdowns occasioned by internal friction. In addition, the viscosity of silicone oil placed inside a partially inflated lumen imparts a consistency to the structure which closely predicates natural breast tissue.

Despite its widespread acceptance, the use of silicone oil does present several major disadvantages. One such disadvantage involves the inability of the body to eliminate silicone oil. The silicone oil continually migrates through the wall of the implant into surrounding tissue where, because is not eliminated by the body, it can accumulate and produce a painful inflammatory reaction. In the case of traumatic rupture of the shell, silicone is forced into the surrounding tissues, travelling down the facial planes where it causes a severe foreign body reaction and requires extensive surgery to remove. An additional drawback with respect to silicone oil is that it is radiographically dense. This makes it more difficult to examine the area of implant by x-ray, or the like. This may obscure mammogram detail and delay detection of breast cancer.

SUMMARY OF THE INVENTION

In accordance with the present invention, many of the drawbacks associated with prior implant prostheses are solved by the provision of a unique gel filler system for implant lumens which combines the advantages of silicone oil, while, at the same time, eliminating the drawbacks discussed above. The gel of the present invention combines a bio-compatible, excretable polymeric material, in a solution of a bio-compatible salt. One such material is a form of polyvinylpyrollidone preferably having the general empirical formula $[(CHCH_2)_2N(CH_2)_3CO]_n$ wherein $n \approx 25-500$ and otherwise known and marketed as Plasdone TM (Trademark of GAF Corporation New York, New York) in a gel system, including a salt solution in a solvent material, in a unique manner. The relative amounts of Plasdone TM and salt along with the salt composition can be varied in the gel of the present invention to produce the desired osmotic potential, viscosity and radiodensity compatible with a particular prothesis application. The vast majority of such combinations are completely excretable by the body and, present no danger of foreign body reaction. The invention contemplates the combination of Plasdone TM of the desire molecular weight with a bio-compatible salt which is preferably one which enhances the radiolucent nature of the gel material, although this is not, in itself, necessarily a limiting factor.

Preferred salts include sodium lactate and sodium acetate. While other salts can be used including sodium chloride, for example, it is somewhat less desirable because of its lower radio translucency due to the higher atomic number of chlorine. Also, although other cation salts such as those of calcium and potassium could be used, sodium salts are preferred because sodium is the most bio-compatible cation. The radiolucency of the salt is related to the cube of the atomic number of the constituents, so those containing atoms with atomic numbers similar to natural tissue are much preferred.

The gel is normally made by dissolving the desired concentration of salt in the deionized, sterilized water and adding the Plasdone TM to create the desired osmotic potential or osmolarity. For most applications this is adjusted to coincide with that of a normal body. However, other osmotic potentials may be utilized as desired for other situations. The desired amount of the combined gel is then sealed within the lumen prior to implant.

Two representative formulations which have the viscosity and lubricating ability within the osmolarity range of 250-350 milliosmoles are listed below:

1. 436 gms Plasdone TM (mw 40,000) combined with 23.0 gms sodium acetate and 1 liter of deionized water.
2. 878 gms Plasdone TM (mw 12,000) combined with 17.78 gms sodium acetate and 1 liter of deionized water.

DESCRIPTION OF THE PREFERRED EMBODIMENT

The present invention contemplates a combination of a bio-compatible or excretable polymer material with a salt solution in a solvent such as deionized water as a gel material for filling implant lumens. The combination and choice of materials is limited only by certain fundamental and desired factors. These include the ability of the body to metabolize and/or excrete the combination including the polymer gel and salt material, the ability of the combination of constituents to impart acceptable viscosity and lubrication properties, and the ability of the combination of constituents to equal or very nearly equal the osmolarity of the body (250-350 milliosmoles). It is further desired that the combination have radiolucency similar to normal breast tissue or equivalents.

While bio-compatible excretable polymer materials can be used, known suitable bio-compatible excretable polymer materials include Dextran of a suitable molecular weight (approximately 50,000) and Hetastarch (hydroxyethyl starch). The preferred material has long been accepted as a bio-compatible material and produces very good results in the gel combination of the invention. Like silicone oil, this material has superior lubricating properties to ensure maximum shell life and avoid shell breakdown due to internal friction. The polymer materials enumerated above, of molecular weights normally contemplated for the gels of the invention, are not toxic to the system of the implant patient. If an implant were to rupture, however, the gel should preferably be removed from the body and this can be done, at least in part, by irrigation of the tissues at the time the silicone shell is removed. The remaining gel material will be removed by the reticuloendothelial system and excreted through the kidneys. Very high molecular weight polymers may present a problem with respect to elimination. The highest known molecular weight of excreted Plasdone TM polymer material is in the range of 87,000 to 104,000 and, for this reason, the recommended molecular weight of the preferred embodiment should be below this range.

A salt is added to the polymer in the gel to assure that the proper or desired osmotic properties or osmolarity is achieved and maintained for the system. For most applications, the gel is made osmotically equivalent to the normal osmolarity of the body (250-350 milliosmoles). Deviation from this, however, may desirable for certain specialized applications. With respect to the selection of the salt material two important considerations should be weighed. One is the relative radiolucency or permeability of the material to x-rays. The other is the ability of the body to eliminate the material should leakage occur. With respect to the radiolucency, in order to evaluate the female breast for development of small tumors, current practice is to regularly obtain x-ray mammograms. This is done by flattening the breast onto a horizontal radiographic plate and exposing it to an x-ray source for a standard exposure. It is well-known in the art to use 4cm thick acrylic block as a breast tissue equivalent material to determine x-ray penetrance and optical density on the resultant processed x-ray film.

As explained below, mammary implants with silicone gels are not penetrated well by x-rays because of silicone's high atomic number. This is detrimental when evaluating a breast for new tumors with mammography, as the silicone renders the processed x-ray film contrast unacceptable for evaluating underlying breast tissue. Saline filled prosthetics are an improvement over silicone gel filled prosthetics, but they also cause overexposure of surrounding breast tissue on processed x-ray film, obscuring the breast tissues. Normal saline filled implants at standard mammographic x-ray exposures result in x-ray film with an optical density of less than 1.2, and an x-ray penetrance of 9.2 milliroentgens. If one developed a gel filler that had a lower x-ray density than that of normal tissue, this would result in under-exposure of the x-ray film and great loss of tissue detail surrounding the implant. Thus, a material having an x-ray density close to that of normal tissue is most desirable. The ideal material range produces an optical density from about 1.2-1.3 and an x-ray penetrance of from 9.2 to about 30 milliroentgens.

One of the advantages of the gel of the present invention is that it is generally more radiolucent than previous gels or normal saline. The bio-osmotic gel of the invention is designed to have an x-ray density close to that of natural breast tissue, thus allowing improved tissue discrimination and improved detection of very small tumors. Typical x-ray film penetrance for the gel of the invention is in a range from a value just greater than 9.2 milliroentgens through about 30.0 milliroentgens. This corresponds to a resultant optical density of the processed x-ray film of from 1.2 to 1.3.

It is a generally established principle that the radiodensity of a pure material is directly proportional to the atomic number of that material cubed ($Z^3$). For multiple species molecules, the atomic number of each element contributes a proportioned amount. Thus, salts using lower atomic number elements as constituents are generally preferred over those using elements having higher atomic numbers. For example, a saline filled implant would be an implant including a salt (NaCl) having equal numbers of sodium and chlorine atoms with atomic numbers of 11 and 17 respectively. The relatively high atomic number of chlorine renders the implant less radiolucent than is desired. Although in the combination of the present invention, saline has been found to exhibit better translucence than in previous combinations. The preferred implant gels in accordance with the present invention use a combination of polymer and sodium acetate, or sodium lactate. Sodium acetate has the lowest total "Z" value of the three.

Another consideration with respect to selection of the salt involves the ease of assimilation of the material into the body and elimination, should leakage or rupture occur. For example, solutions containing large amounts of calcium or potassium salts could be used, but they would be more likely to cause cardiac conduction problems in the tissue of patients. Sodium has been chosen as the preferred cation because it is the most extracellularly abundant bodily cation. It is otherwise quite acceptable for the gel and it is less radiopaque than other usable alkali or alkaline earth cations.

A very high molecular weight polymer, as stated above, is undesirable from the standpoint of difficulty of the body to eliminate it. Fortunately, in general the most desirable molecular weights of polymer in accordance with the preferred embodiments are considerably below 85,000. For example, in regard to breast implants, a molecular weight in the vicinity of 40,000 is preferred because it provides desired viscosity and lubricating quality to fulfill other qualities of material.

Two suitable formulas which have acceptable viscosity and lubricating ability at the midpoint of correct normal osmolarity are as follows:

1. 436 gms polymer (mw 40,000) combined with 23.0 gms sodium bicarbonate and 1 liter of deionized water (approximately 296 milliosmoles).

2. 878 gms polymer (mw 12,000) combined with 17.78 gms sodium acetate and 1 liter of deionized water (approximately 296 milliosmoles).

Other combinations, of course, would occur to those skilled in the art and the formulation may well depend on the particular application of the implant. The particular combinations presented in this specification are disclosed as being exemplary of many possibilities and not meant to be limiting of the invention in any sense.

What is claimed is:

1. A radiolucent bio-osmotic gel medium for filling an implant lumen comprising:
 a bio-compatible organic polymer in a solution of bio-compatible salt of relatively low Z number;
 wherein the organic polymer material of the gel medium is one excretable by the body;
 wherein the gel medium is further characterized by having an osmolarity of from about 250 milliosmoles to about 350 milliosmoles; and
 wherein the gel medium has an x-ray absorption under standard exposure approximately equal to that of breast tissue, such that processed mammographic x-ray film will result in an optical density on the x-ray film or 1.2–1.3 and a range of average penetrance from a value greater than 9.2 milliroentgens, to a value of 30 milliroentgens.

2. A radiolucent bio-osmotic gel medium for filling an implant lumen comprising:
 a bio-compatible organic polymer in a solution of bio-compatible salt;
 wherein the organic polymer material of the gel medium is one excretable by the body and wherein the gel medium has an x-ray absorption under standard exposure approximately equal to that of breast tissue, such that processed mammographic x-ray film will result in an optical density on the x-ray film of 1.2–1.3 and having a range of average penetrance from a value greater than 9.2 milliroentgens, to a value of 30.0 milliroentgens.

3. The radiolucent bio-osmotic gel medium of claim 2 wherein the organic polymer material comprises an amount of a polymer of the empirical formula $[(CHCH_2)_2N(CH_2)_3CO]_n$ wherein "n" is a number from about 25 to 500.

4. The radiolucent bio-osmotic gel medium of claim 2 being further characterized by having an osmolarity of rom about 250 milliosmoles to about 350 milliosmoles.

5. The radiolucent bio-osmotic gel medium of claim 2 wherein the solution of bio-compatible salt is an aqueous solution of an organic sodium salt.

6. The radiolucent bio-osmotic gel medium of claim 3 wherein the solution of bio-compatible salt is an aqueous solution of an organic sodium salt.

7. The radiolucent bio-osmotic gel medium of claim 5 wherein the sodium salt is selected for the group consisting of sodium bicarbonate, sodium acetate and sodium lactate.

8. The radiolucent bio-osmotic gel medium of claim 6 wherein the sodium salt is selected from the group consisting of sodium bicarbonate, sodium acetate and sodium lactate.

9. The radiolucent bio-osmotic gel medium of claim 7 wherein the salt is sodium acetate.

10. The radiolucent bio-osmotic gel medium of claim 8 wherein the salt is sodium acetate.

11. The radiolucent bio-osmotic gel medium of claim 9 wherein the concentration of sodium acetate is from about 0.11 M to about 0.4 M.

12. The radiolucent bio-osmotic gel medium of claim 10 wherein the concentration of sodium acetate is from about 0.11 M to about 0.4 M.

13. A radiolucent bio-osmotic gel for filling an implant prosthesis comprising:
 an amount of a polymer excretable by the body of the empirical formula $[(CHCH_2)_2N(CH_2)_3CO]_n$ having an average molecular weight of 85,000 or less, and an aqueous solution of sodium acetate; and
 wherein the gel material comprises 436 gms of the polymer (mw 40,000) combined with 23.0 gms of the sodium acetate in one liter of deionized water and wherein the osmolarity of the gel medium is between about 250 milliosmoles and 350 milliosmoles.

14. A radiolucent bio-osmotic gel for filling an implant prosthesis comprising:
 an amount of a polymer excretable by the body of the empirical formula $[(CHCH_2)_2N(CH_2)_3CO]_n$ having an average molecular weight of 85,000 or less, and an aqueous solution of sodium acetate; and
 wherein the gel material comprises 878 gms of the polymer (mw 12,000) combined with 17.78 gms of the sodium acetate in one liter of deionized water and wherein the osmolarity of the gel medium is between about 250 milliosmoles and 350 milliosmoles.

15. A radiolucent bio-osmotic gel for filling an implant prosthesis comprising an amount of a polymer excretable by the body of the empirical formula $[(CHCH_2)_2N(CH_2)_3CO]_n$ having an average molecular weight of 85,000 or less, and an aqueous solution of a sodium salt of relatively low Z number selected from the group consisting of sodium bicarbonate, sodium acetate and sodium lactate, wherein the osmolarity of the gel medium is between about 250 milliosmoles and 350 milliosmoles and wherein the gel material has an x-ray absorption under standard exposure approximately equal to that of breast tissue, such that processed mammographic x-ray film will result in an optical density on the x-ray film of 1.2–1.3 and having a range of average penetrance from a value greater than 9.2 milliroentgens, to and including 30.0 milliroentgens.

* * * * *

UNITED STATES PATENT AND TRADEMARK OFFICE
CERTIFICATE OF CORRECTION

PATENT NO. : 5 067 965

DATED : November 26, 1991

INVENTOR(S) : Robert A. Ersek, et al

It is certified that error appears in the above-identified patent and that said Letters Patent is hereby corrected as shown below:

In column 5, line 41, delete "rom" and insert -- from -- .

Signed and Sealed this

Sixteenth Day of March, 1993

Attest:

STEPHEN G. KUNIN

*Attesting Officer*   Acting Commissioner of Patents and Trademarks